(12) United States Patent
Becq et al.

(10) Patent No.: US 8,242,136 B2
(45) Date of Patent: *Aug. 14, 2012

(54) USE OF GLUCOSIDASE INHIBITORS FOR THERAPY OF MUCOVISIDOSIS

(75) Inventors: Frédéric Becq, Poitiers (FR); Caroline Norez, Saint Priest (FR)

(73) Assignees: Centre National de la Recherche Scientifique (C.N.R.S.), Paris (FR); Universite de Poitiers, Poitiers (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/116,482

(22) Filed: May 26, 2011

(65) Prior Publication Data

US 2011/0269795 A1    Nov. 3, 2011

Related U.S. Application Data

(63) Continuation of application No. 10/578,328, filed as application No. PCT/FR2004/002858 on Nov. 5, 2004, now Pat. No. 7,973,054.

(30) Foreign Application Priority Data

Nov. 7, 2003    (FR) ...................................... 03 13134

(51) Int. Cl.
  *A61K 31/445*    (2006.01)
(52) U.S. Cl. ...................................... 514/315; 514/851
(58) Field of Classification Search ................... 514/315
  See application file for complete search history.

(56) References Cited

U.S. PATENT DOCUMENTS

| 4,639,436 | A | 1/1987 | Aktiengesellschaft et al. |
| 6,200,958 | B1 | 3/2001 | Odaka et al. |
| 2002/0035072 | A1 | 3/2002 | Asano et al. |
| 2004/0081711 | A1 | 4/2004 | Rao |
| 2004/0171674 | A1 | 9/2004 | Rao |

FOREIGN PATENT DOCUMENTS

| WO | WO 98/20123 A | 5/1998 |
| WO | WO 01/02586 A | 1/2001 |
| WO | WO 01/02862 A | 1/2001 |
| WO | WO 01/21769 A | 3/2001 |
| WO | WO 03/037265 | 5/2003 |
| WO | WO 2004/069190 A | 8/2004 |

OTHER PUBLICATIONS

Andersson et al., "Activation of CFTR by Genistein in Human Airway Epithelial Cell Lines," Biochemical and Biophysical Research Communications, vol. 308, No. 3, pp. 518-522, XP004444570, ISSN: 0006-291X, Aug. 29, 2003.

Ganan S. et al., "A major proportion of N-Glycoprotiens are transiently glucosylated in the endoplasmic reticulum", Biochemistry, 1991, p. 3098-3104, vol. 30, No. 12.

Karlsson G. et al., "Effects of the imino sugar N-butyldeoxynojirimycin on the N-Glycosylation of Recombinant gp 120", Journal of Biological Chemistry, 1993, p. 570-576, vol. 268, No. 1.

Trombetta S. et al., "Purification to apparent homogeneity and partial characterization of Rat Liver UDP-Glucose;Glycoprotein Glucosyltransferase", Journal of Biochemistry, 1992, p. 9236-9240, vol. 267, No. 13.

Riddle. MC. AM. Fam. Physician (1990), 60(9), 2613-20.

Dwek et al., "Targeting Glycosylation as a therapeutic approach", Jan. 2002, Nature Reviews Drug Discovery, vol. 1, p. 65-75.

Platt F. et al., "N-Butyldeoxygalactonojirimycin inhibits Glycolipid Biosynthesis but does not affect N-linked Oligosaccharide Processing", Journal of Biological Chemistry, 1994, p. 27108-27114, vol. 269, No. 43.

Asano (Reprint), "Glycosidase inhibitors: update and perspectives on practical use," Glycobiology, vol. 13, No. 10, pp. 93R-104R, Publisher: Oxford Univ Press Inc, Journals Dept, 2001 Evans Road, Cary, NC 27513 USA. ISSN: 0959-6658, XP008031797, Oct. 1, 2003.

*Primary Examiner* — James D Anderson
*Assistant Examiner* — Gregg Polansky
(74) *Attorney, Agent, or Firm* — Young & Thompson

(57) ABSTRACT

A treatment of cystic fibrosis by administration of a pharmaceutically acceptable amount of the glucosidase inhibitor NB-DMJ (N-butyldeoxy-mannojirimycin).

4 Claims, 7 Drawing Sheets

USE OF GLUCOSIDASE INHIBITORS FOR THERAPY OF MUCOVISIDOSIS

CROSS REFERENCE TO RELATED APPLICATIONS

Figure 1:
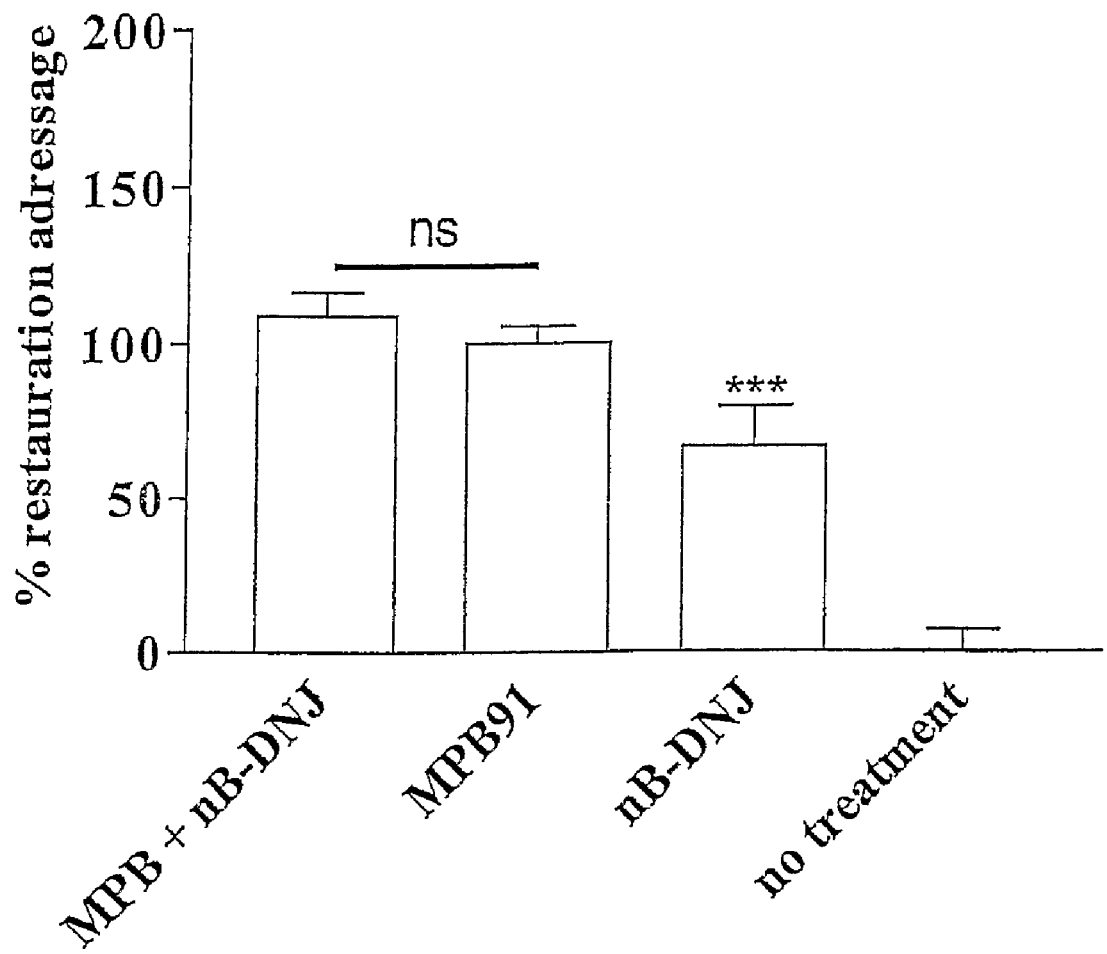

This application is a continuation of application Ser. No. 10/578,328 filed on Jan. 22, 2007; which is the 35 U.S.C. 371 national stage of International application PCT/FR2004/002858 filed on Nov. 5, 2004; which claimed priority to French application 03/13134 filed Nov. 7, 2003. The entire contents of each of the above-identified applications are hereby incorporated by reference.

BACKGROUND OF THE INVENTION

A subject of the present invention is the use of glucosidase inhibitors for the preparation of medicaments for the treatment of cystic fibrosis.

Cystic fibrosis (CF) is the most widespread lethal, autosomal, recessive genetic disease in European and North American populations. The CF gene (locus 7q31) encodes the transmembrane protein named CFTR (for *Cystic Fibrosis Transmembrane Conductance Regulator*) (Tsui et al., 1985; Riordan et al., 1989). Mutations of the CF gene cause an abnormal transport of water and electrolytes through the cell membranes of various organs such as the lungs, sudoriparous glands, intestine and exocrine pancreas. Although more than 1000 mutations of the CFTR protein exist, the most frequent mutation (70% of patients) is the deletion of a phenylalanine in the NBF1 domain in position 508 (delF508). The main cause of mortality in CF patients is linked to this deletion and leads to infections or to pulmonary insufficiency caused by an increase in the viscosity of the mucus. This viscosity leads the occlusion of the respiratory tracts and increases the risk of infections by opportunist bacteria. An aggravation is moreover noted in the digestive and in particular pancreatic system (patient with pancreatic insufficiency). The CFTR protein is a glycoprotein of 1480 amino acids, belonging to the ABC membrane transporter superfamily. CFTR is a chlorine channel located in the apical plasmic membrane of the pulmonary epithelial cells in healthy individuals. CFTR is responsible for the transepithelial transport of water and electrolytes and in a healthy individual allows the hydration of the pulmonary airways. In CF patients, this protein is absent from the plasmic membranes due to incorrect addressing of the protein which is retained in the endoplasmic reticulum (ER). The hydration of the pulmonary airways is no longer functional in this case. The delF508 deletion upsets the folding of the NBF1 domain and prevents the complete maturation of the protein which is therefore degraded very early during its biosynthesis. However, if the delF508 protein reaches the membrane, it functions as a chloride channel. One of the keys to a treatment of this disease is therefore a readdressing of delF508 towards the cell membrane. Once at the membrane, the delF508 transport activity can be stimulated by endogenous or exogenous physiological agonists.

The mechanism for addressing the CFTR protein is implemented as follows. After its neosynthesis, the CFTR protein is found in the ER lumen where it undergoes various glycosylations by means of glycosyl transferases. The protein is found with inter alia 3 N-linked glucoses and 1 N-linked mannose. Two of the glucoses are removed by glucosidases I and II. Calnexin or calreticulin, dependent calcium chaperones, recognize the monoglucosylated protein and bind to the latter via the N-linked glucose. These chaperones prevent the different CFTR proteins present in the ER from aggregating together and allow the binding of other chaperones such as ERp57. The CFTR/Calnexin/ERp57 complex thus formed allows the folding of the CFTR. Then, the glucosidase II removes the remaining glucose, thus releasing the CFTR from the chaperones. If the folding is incorrect, a glucosyltransferase adds a glucose to the CFTR which can once again undergo one or more cycles until it is well folded. If the folding is still incorrect, a mannosidase removes the N-linked mannose, the protein will then be transported into the cytosol, via the translocon channel complex, where it can be degraded (*Ellgard & Helenius*, 2003). This phenomenon is observed for 80% of the CFTR-WT and 99% of the delF508-CFTR. Once in the cytosol, the protein is assisted by different chaperones such as Hsp70, Hsp90 or Hdj-2. These chaperones allow the ubiquitin to bind to the CFTR. Thus labelled, the CFTR is recognized and degraded by the 26S proteasome complex which is ATP-dependent (*Gelman* et al., 2002). If the folding of the CFTR is considered correct by the reticulum control mechanism, the protein can reach the Golgi apparatus. It is assisted by the "cargo" protein ERGIC-53 (belonging to the lectin family) which binds to the CFTR via the mannose. The passage of the ERGIC takes place via vesicles formed by the factor COP I (*Ellgard & Helenius*, 2003). It seems that if the protein is badly folded, it is sensitive to the endoglycosidase H of the Golgi apparatus (*Cheng* et al., 1990) and is then returned the reticulum where it is degraded. On the other hand, the correctly folded protein, which is resistant to endoglycosidase H, is assisted by the factor VIP 36 (homologue of ERGIC-53) and conveyed to the apical membrane (*Fiedler & Simons*, 1995).

Whilst it has already been observed that a glucosidase inhibitor, castanospermine, had an effect on the renewal of the presence of delF508 at the surface of pulmonary epithelial cells (Wei et al., 1996), on the other hand it has never been described that this compound was capable not only of restoring the membrane addressing of delF508, but also of allowing delF508 to function as an ion transporter. The authors of this article had therefore formulated no hypothesis as to the possible use of this compound within the framework of the treatment of cystic fibrosis.

The Inventors have precisely studied these glucosidase inhibitors in order to determine whether they were capable both of ensuring the correct and specific addressing of delF508 without however affecting its ion transporting activity or the cell viability.

N-butyl-deoxynojirimycin (NB-DNJ), is a glucosidase I and II inhibitor of the endoplasmic reticulum, which was first developed as an anti-viral molecule for humans. The inhibition of these enzymes modifies the folding of a glycoprotein of the envelope of the HIV virus (Human Immunodeficiency Virus) and as a result, the virus cycle is found to be blocked (Platt et al., 2001). A therapy using NB-DNJ has been evaluated on patients suffering from acquired immunodeficiency syndrome: this molecule is well tolerated and is not cytotoxic on tissues in culture even at a high concentration (2 mM). Moreover, these clinical trials revealed that NB-DNJ also had an inhibiting effect on the glucosyltransferases. This is why this molecule, also named OGT 918, has been studied in the treatment of Gaucher's disease (*Dwek* et al., 2000, *Cox* et al., 2000). This genetic disease is caused by a deficiency of the lysosomal enzyme, β-glucocerebrosidase, which leads to an accumulation of glucocerebrosides (enzyme substrate). NB-DNJ, a glucosyltransferase inhibitor involved in the biosynthesis of the glucocerebrosides, thus prevents their synthesis and accumulation (*Dwek* et al., 2000, *Cox* et al., 2000). NB-DNJ obtained market authorisation as a medicament for Gaucher's disease under the name of Zavesca® in 2002.

The present invention results from the demonstration by the Inventors, of the fact that NB-DNJ, and other glucosidase inhibitors in general, are capable of restoring the membrane addressing of delF508 without altering the other chloride channels, and allow delF508 to function as an ion transporter.

A subject of the present invention is the use of glucosidase inhibiting compounds for the preparation of a medicament intended for the treatment of cystic fibrosis.

By the expression "glucosidase inhibitor" is meant any glucosidase I and/or II inhibitor, the inhibition of these glucosidases being able to be measured in particular according to the method described in Platt et al., 1994.

A subject of the present invention is more particularly the abovementioned use of glucosidase-inhibiting compounds, said compounds being selected from those capable of restoring the membrane addressing of delF508 without altering the other chloride channels, and allowing delF508 to function as an ion transporter, in particular within the framework of experiments described hereafter carried out on human homozygous pulmonary epithelial CF15 cells for the deletion delF508.

More particularly a subject of the invention is the abovementioned use of glucosidase inhibiting compounds chosen from the compounds of general formula (I) below:

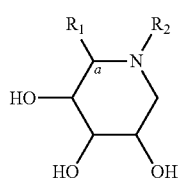

(I)

in which $R_1$ represents a $CH_3$, or $CH_2OH$ group, $R_2$ represents H or an alkyl group with 1 to 5 carbon atoms, or $R_1$ and $R_2$ form together with the carbon in position (a) and the nitrogen of formula (I) above a group of formula:

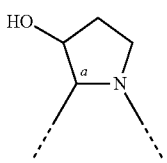

More particularly the invention relates to the abovementioned use of the compounds of formula (I) below:

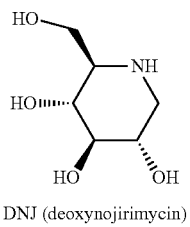

DNJ (deoxynojirimycin)

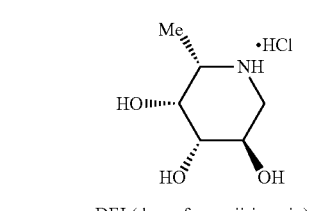

DFJ (deoxyfuconojirimycin)

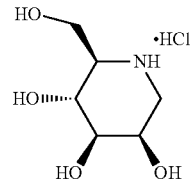

DMJ (deoxymannojirimycin)

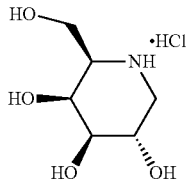

DGJ (deoxygalactonojirimycin)

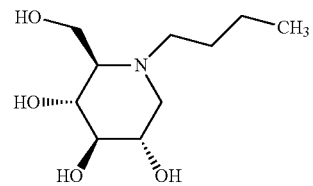

NB-DNJ (N-butyl-deoxynojirimycin)

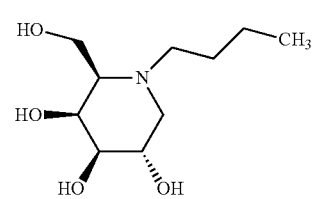

NB-DGJ (N-butyl-deoxygalactonojirimycin)

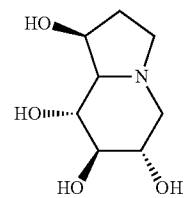

Castanospermine

More particularly the invention relates to the abovementioned use of glucosidase inhibitors chosen from the compounds of general formula (II) below:

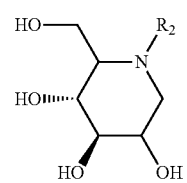

(II)

in which $R_2$ represents H or an alkyl group with 1 to 5 carbon atoms.

More particularly a subject of the invention is the abovementioned use of glucosidase inhibitors as defined above, chosen from the compounds of general formula (IIa) below:

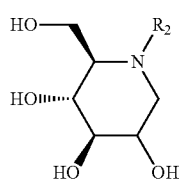

(IIa)

in which $R_2$ represents H or an alkyl group with 1 to 5 carbon atoms.

A subject of the invention is also the abovementioned use of glucosidase inhibitors according to one of claims 1 to 4, chosen from the following compounds of general formulae (II.1) or (II.2):

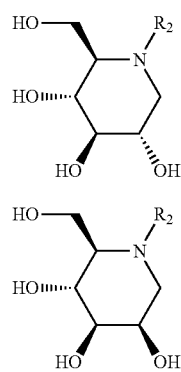

in which $R_2$ represents H or an alkyl group with 1 to 5 carbon atoms.

More particularly the invention relates to the abovementioned use of the compounds of formulae (II.1) or (II.2) as defined above in which $R_2$ represents H or an N-butyl group below:

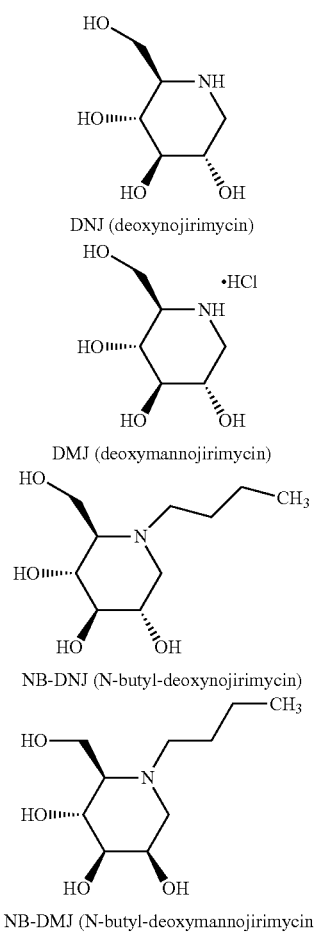

Preferably, the compounds used within the framework of the present invention are NB-DNJ and NB-DMJ.

Preferably also, the compound used within the framework of the present invention is NB-DNJ.

A subject of the invention is also the abovementioned use of glucosidase inhibiting compounds defined above, for the preparation of a medicament which can be administered by oral (syrup, suspension, gelatin capsules, tablets, powder or granules), rectal (suppositories), nasal route (aerosol by inhalation, or drops), in particular at a rate of approximately 1 mg to 2 g per day of active ingredient for adults, or 1 mg to 1 g per day for children and infants, in one or more doses.

The invention also relates to the abovementioned use of glucosidase inhibiting compounds defined above in combination with a CFTR channel activating compound.

A subject of the invention is therefore more particularly the abovementioned use of glucosidase inhibiting compounds defined above in combination with a CFTR channel activating compound chosen from:

genistein of the following formula:

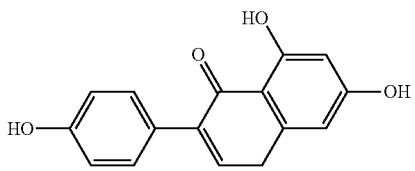

or the derivatives of the benzo[c] quinoliziniums of formula (II) below:

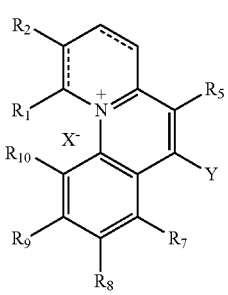

in which:
- $R_1$ and $R_2$ represent a hydrogen atom, or form in combination with $C_1$ and $C_2$ an aromatic ring with 6 carbon atoms,
- $R_5$ represents a hydrogen atom, or a linear or substituted alkyl group with 1 to 10 carbon atoms, in particular a butyl group, or an ester of formula COOR' in which R' represents a linear or substituted alkyl group with 1 to 10 carbon atoms, in particular an ethyl group,
- Y represents an —OH, —SH, —NH$_2$, or —NHCOCH$_3$ group,
- $R_7$, $R_8$, $R_9$ and $R_{10}$ represent a hydrogen atom, or at least one of $R_7$, $R_8$, $R_9$ or $R_{10}$, represents a halogen atom, in particular a chlorine, bromine or fluorine atom,
- X represents a halogen atom in anionic form, in particular a bromine Br⁻, or chlorine Cl⁻ atom, or a group of atoms in anionic form.

More particularly a subject of the invention is the abovementioned use of glucosidase inhibiting compounds defined above in combination with derivatives of the benzo[c] quinoliziniums of formula (II) chosen from the compounds below:

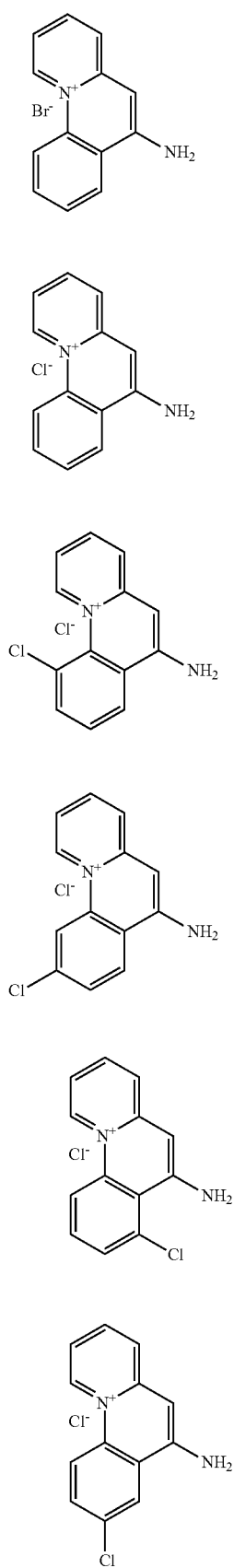
compound 13 (MPB-01)
compound 11 (MPB-26)
compound 14 (MPB-02)
compound 15 (MPB-03)
compound 16
compound 17
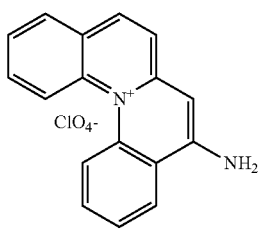
compound 22
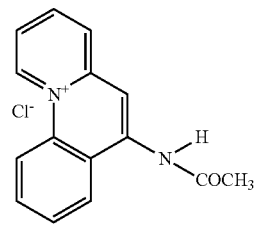
compound 23
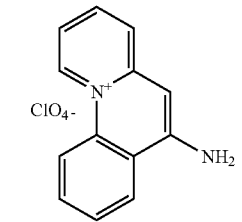
compound 24
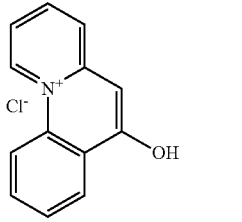
compound 12 (MPB-05)
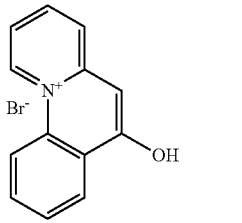
compound 18 (MPB-06)
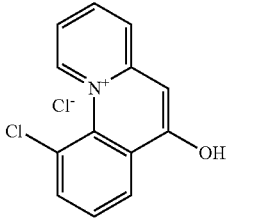
compound 19 (MPB-07)
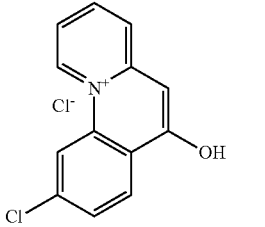
compound 20 (MPB-08)

compound 21 (MPB-27)
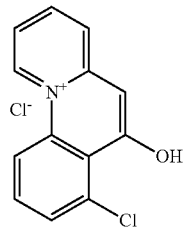
compound 25 (MPB-30)
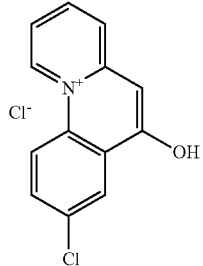
compound 26 (MPB-29)
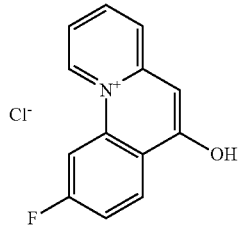
compound 27 (MPB-32)
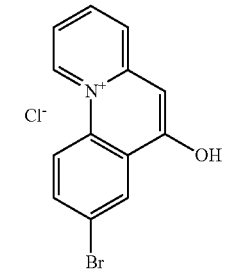
compound MPB-91
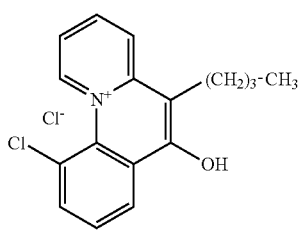
compound MPB 73
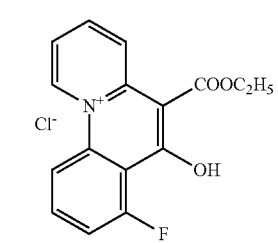
compound MPB 75
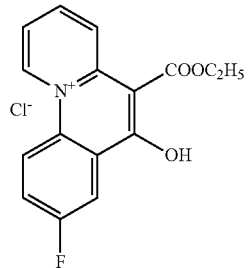
compound MPB 86
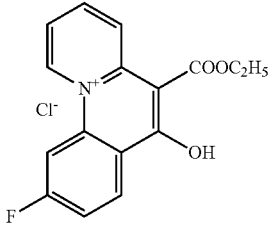
compound MPB 77
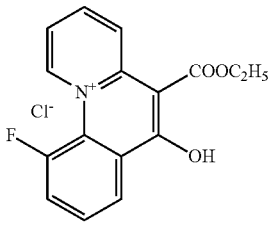
compound MPB 87
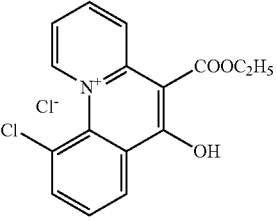
compound MPB 88
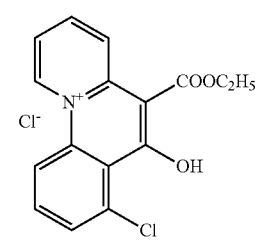
compound MPB 102

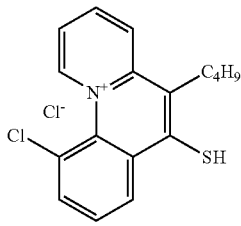
compound MPB 103

A subject of the invention is also the products comprising at least one glucosidase inhibiting compound, in particular a compound of formula (I) or (II) as defined above, and at least one CFTR channel activating compound as defined above, as combination products for a simultaneous or separate use or use spread over time, in cystic fibrosis therapy.

The invention is further illustrated by means of the detailed description which follows of the experimental demonstration of the effect of correct and specific addressing of delF508 by MB-DNJ, without the latter however affecting either its ion transporting activity or the cell viability.

I) MATERIAL AND METHODS

M1. Cell Culture

CHO-WT cells: CHO (Chinese Hamster Ovary) cells are fibroblasts which have been transfected with the wild-type CFTR gene (CFTR-WT). These cells will therefore overexpress the CFTR protein.

Culture medium: MEM alpha medium (GIBCO)+7% foetal calf serum+0.5% penicillin/streptomycin+100 µM of Methothrexate (Amethopterin, Sigma)

CF15 cells: CF15 cells are human epithelial cells of nasal origin which express the ΔF508-CFTR gene.

Culture medium: DMEM medium+HAM F12+10% FCS+ 0.6% penicillin/streptomycin+growth factors (insulin 5 µg/ml, transferrin 5 µg/ml, epinephrine 5.5 µM, adenine 0.18 mM, EGF 10 µg/ml, T3 2 nM, Hydrocortisone 1.1 µM)

Calu-3 cells: Calu-3 cells are human epithelial cells of pulmonary origin which express the wild-type CFTR gene.

Culture medium: DMEM medium/F12 with glutamax+7% foetal calf serum+1% penicillin/streptomycin M2. Immunolabelling Immunolabelling makes it possible to visualize the cell location of the CFTR protein by means of an anti-CFTR primary antibody (Ab) then a primary anti-antibody secondary antibody labelled with Cy3 fluorophore. The cells are previously seeded on lamellae in appropriate culture medium. 3 washings with TBS (NaCl: 157 mM, Tris base: 20µM, pH 7.4) of 5 minutes each are carried out. The cells are then fixed by the addition of TBS-paraformadehyde (3%) over 20 minutes. After 3 washings with TBS (5 minutes), the cells are incubated with 0.1% TBS-triton (10 minutes) which allows the formation of holes in the cell membrane, then 3 washings with TBS are once again carried out before bringing the cells together with 0.5% TBS-BSA-0.05% saponin for 1 hour. The cells are then incubated with the CFTR anti-C terminal primary antibody (2µg/ml) for 1 hour. 3 washings with TBS-BSA-saponin of 5 minutes each are carried out before incubation with the GAM-cy3 secondary antibody (1/400) for 1 hour. Following two 5-minute washings with TBS, the nuclei are labelled by incubation with Topro3 (1/1000) for 5 minutes. Finally, the lamellae can be mounted on slides after three last 5-minute washings with TBS. The slides are observed with a confocal microscope (Bio-Rad) by means of excitation with a laser at appropriate wavelengths. In order to differentiate between Cy3 and Topro3 labelling the colour of fluorescence of Topro3 has been changed to blue (colour of the nuclei).

M3. Radiotracer Efflux

The measurements of chloride ion transport in the cells were carried out using the radioactive iodide efflux technique (Becq et al., 1999; Dormer et al., 2001). The tracer ($^{125}$I) is incorporated into the intracellular medium. Then, the quantity of radiotracer leaving the cell is counted after the addition of different pharmacological agents. The iodide is used as a tracer of the chloride ion transport. It has been shown that the two radiotracers $^{125}$I and $^{36}$Cl could be considered as equivalents for measuring the activity of a chloride channel (Venglarick et al., 1990). $^{125}$I moreover has the advantage of having a short life compared with that of $^{35}$Cl (respective half-lives: 30 days and 300,000 years). The cells are cultured on 24-well plates in an appropriate medium. 2 rinsings with efflux medium (NaCl: 136.6 mM, KCl: 5.4 mM, $KH_2PO_4$: 0.3 mM, $NaH_2PO_4$: 0.3 mM, $NaHCO_3$: 4.2 mM, $CaCl_2$: 1.3 mM, $MgCl_2$: 0.5 mM, $MgSO_4$: 0.4 mM, HEPES: 10 mM, D-glucose: 5.6 mM) are carried out in order to eliminate the dead cells which release the radioactivity in an anarchic manner. Then, the cells are incubated with 500 µl of charge (1 µCi/ml of $^{125}$INa) for 30 minutes for CHO-WT or 1 hour for CF15 and Calu-3. The iodide is in equilibrium on both sides of the cell membrane. The robot (MultiPROBE, Packard) carries out the following stages: The charge medium is rinsed with efflux medium in order to eliminate the extracellular radioactivity. The supernatant is collected every minute in haemolysis tubes and the medium is replaced by an equivalent volume (500 µl). The samples taken in the first 3 minutes are not subjected to the addition of a drug, they make it possible to obtain a stable base line, characterizing the passive exit of the I⁻ ions. The following 7 samples are obtained in the presence of the molecule to be tested. At the end of the experiment, the cells are lysed by the addition of 500 µl of NaOH (0.1 N)/0.1% SDS (30 minutes), thus, the radioactivity remaining inside the cell can be determined. The radioactivity present in the haemolysis tubes is counted in counts per minute (cpm) using a gamma counter (Cobra II, Packard). The results in cpm are expressed in the form of exit speed of radioactive iodide (R) according to the following formula: R (min$^{-1}$)=[ln ($^{125}$I t$_1$)−ln($^{125}$I t$_2$)]/(t$_1$−t$_2$) with $^{125}$I t$_1$: cpm at time t$_1$; $^{125}$I t$_2$: cpm at time t$_2$. This iodide flow is represented in the form of a curve. In order to quantify the exit of iodide due to the administration of the molecule tested, the following relative flow is calculated which makes it possible to be rid of the base flow: Relative speed (min$^{-1}$)=Rpeak−Rbasal. Finally, these results are standardized in order to be able to compare the effects of the different drugs with each other. The results are presented in the form of an average+/−SEM. Student's statistical test is used in order to compare the effects of the drugs with the controls (the values corresponding to P<0.01 are considered statistically significant).

M4. Cytotoxicity Test

The MTT toxicity test is a colorimetric test which is based on the ability of the mitochondrial dehydrogenases to metabolize MTT (yellow tetrazolium salt) to formazan (purple). The absorbance, proportional to the concentration of converted dye, can then be measured by spectrophotometry. The cells are incubated on 96-well plates in the presence of the agent to be tested for 2 hours. 3 controls are carried out: 100% live cells: cells without agent; 0% live cells: cells left in the open air; blank: medium without cells. The cells are rinsed with RPMI medium without phenol red so that the colour of the medium does not interfere with the absorbance measurements. Then they are incubated for 4 hours with 100 µl of RPMI solution supplemented with MTT (0.5 mg/ml). The medium is then eliminated, the addition of 100 μl of DMSO makes it possible to solubilize the converted dye (formazan). The absorbance is measured by spectrophotometry at: 570 nm (purple); 630 nm (background noise). In order to be rid of the background noise, the following calculation is carried out: $OD_{real} = OD_{570\,nm} - OD_{630\,nm}$. Then, the results are standardized with respect to the controls (100% and 0% live cells) and are presented in the form of an average+/−SEM.

II) RESULTS

R1. Effect of NB-DNJ on the Addressing of delF508 in the CF15 Cells

The study of the addressing of the delF508-CFTR protein is carried out in the laboratory by combining the approaches of pharmacology, cell imaging, biochemical and electrophysiological tests on homozygous pulmonary human epithelial CF 15 cells for the deletion delF508. Different molecules exist which are capable of interfering with certain factors involved in the addressing of the CFTR. This is the case with N-butyl-deoxynojirimycin (NB-DNJ) which is a glucosidase I and II inhibitor and which was tested.

For each experiment, the addition of a cocktail (Forskolin 10 μM, Genistein 30 μM) allows the activation of the CFTR when the latter is on the membrane. Thus, an iodide efflux can be observed if the addressing of delF508 has been restored. The results, presented in the form of a histogram have been standardized with respect to a reference treatment (treatment of the cells with 250μM MPB-91 over 2 hours) for which it is considered that there is 100% CFTR activity. We show here that treatment with a glucosidase inhibitor, N-butyldeoxynojirimycin (NB-DNJ) (structure presented below), of the CF15 cells over two hours at 37° C. restores addressing of the delF508 protein and allows the latter to function as an ion transporter (FIG. 1).

Figure 2:
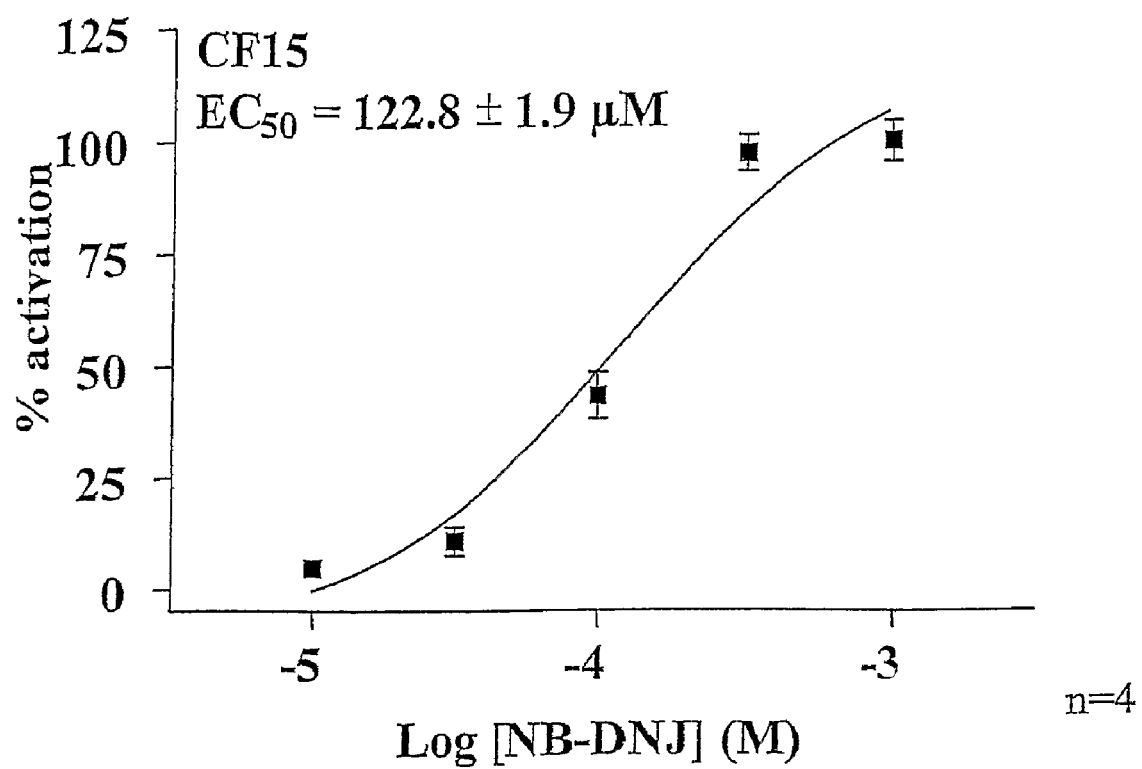

In the absence of treatment of the cells, the delF508 protein is not membranous and there is no iodide efflux stimulated by the cocktail (Forskolin 10μM, Genistein 30 μM). The $EC_{50}$ (concentration of the molecule which produces 50% of maximum effectiveness) of the NB-DNJ was determined at 123 micromol (FIG. 2). By cell imaging we located the delF508 protein in the plasmatic membrane compartments after treatment with NB-DNJ.

R2. Effect of NB-DNJ on the Activity of CFTR in the Calu-3 Cells

In order to show that the effect of NB-DNJ is specific to the addressing of the delF508 and does not alter the other chloride channels, NB-DNJ was tested as potential activator on Calu-3 cells. The results presented in FIG. 3 were obtained in iodide efflux on Calu-3 cells. Our controls are forskolin (5μM, n=8) and MPB-91 (250μM, n=8). NB-DNJ (n=8) is not an activator of the wild-type CFTR nor of other anionic transports of these cells as there is no significant difference between the effect with or without NB-DNJ (basal).

R3. Effect of NB-DNJ on the Addressing of CFTR in the Calu-3 Cells

Figure 4:
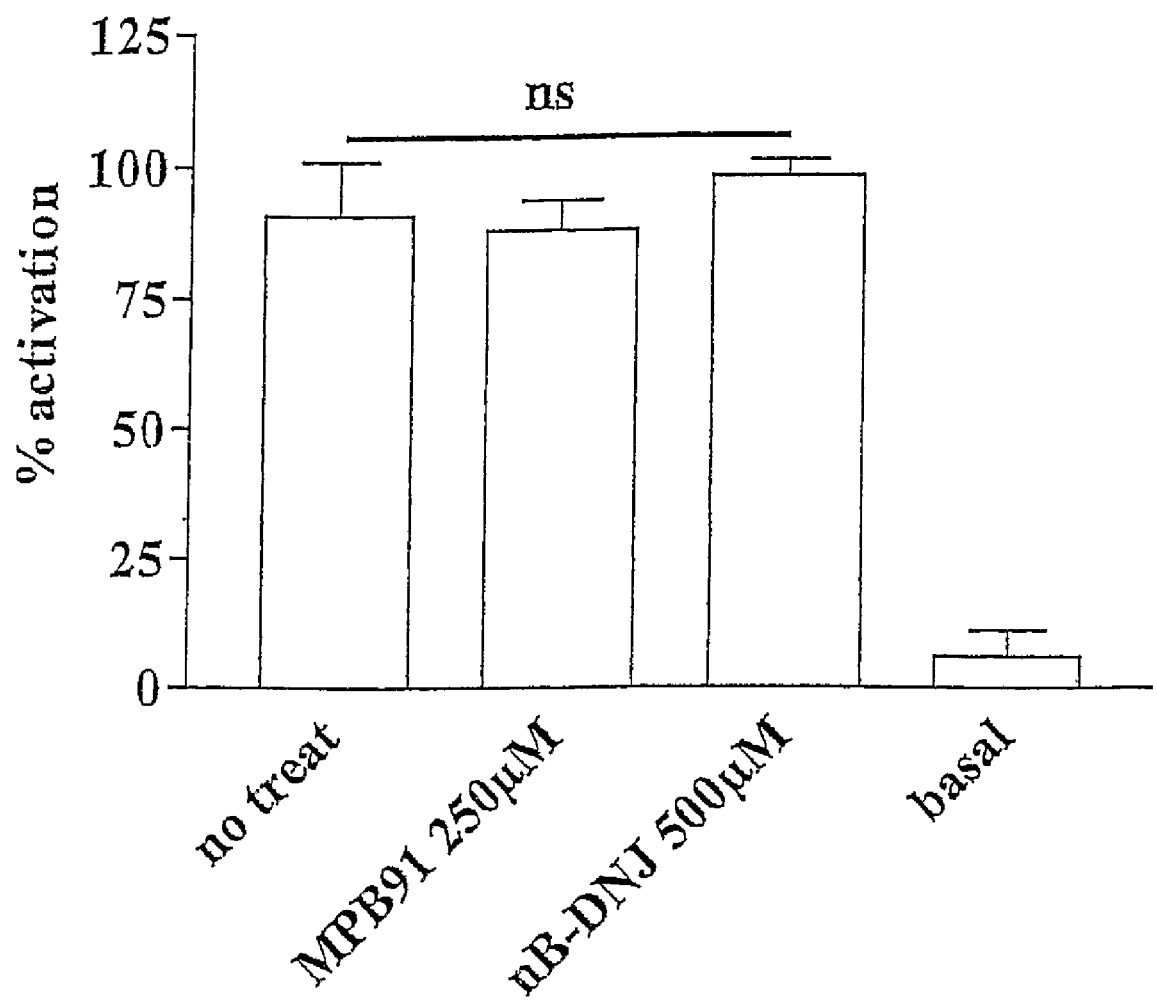

In order to show that the effect of NB-DNJ is specific to the addressing of delF508, NB-DNJ was tested as a modulator of the addressing of the wild-type CFTR on Calu-3 cells. The results presented in FIG. 4 were obtained in iodide efflux on Calu-3 cells treated for 2 hours with NB-DNJ (500μM). In FIG. 4, basal corresponds to cells which are not treated and without stimulation by MPB-91. No iodide efflux is stimulated. The second control corresponds to cells without treatment but stimulated with 250μM of MPB-91. In this case CFTR is activated and an iodide efflux is measured. The third control corresponds to cells treated with MPB-91 for 2 hours at 37° C. then stimulated with 250μM MPB-91. The CFTR activity under this experimental condition is not significantly different compared with the two other experimental situations. Finally, when the Calu-3 cells are treated for 2 hours at 37° C. with 500μM NB-DNJ and stimulated with 250μM MPB-91, the level of CFTR activity is not affected. These results demonstrate that NB-DNJ does not affect the wild-type CFTR addressing route or other chloride channels, nor does it alter the CFTR activity in the human non-CF pulmonary epithelial cells.

R4. Cytotoxicity of the Different Inhibitors of the Addressing Route

Figure 5:
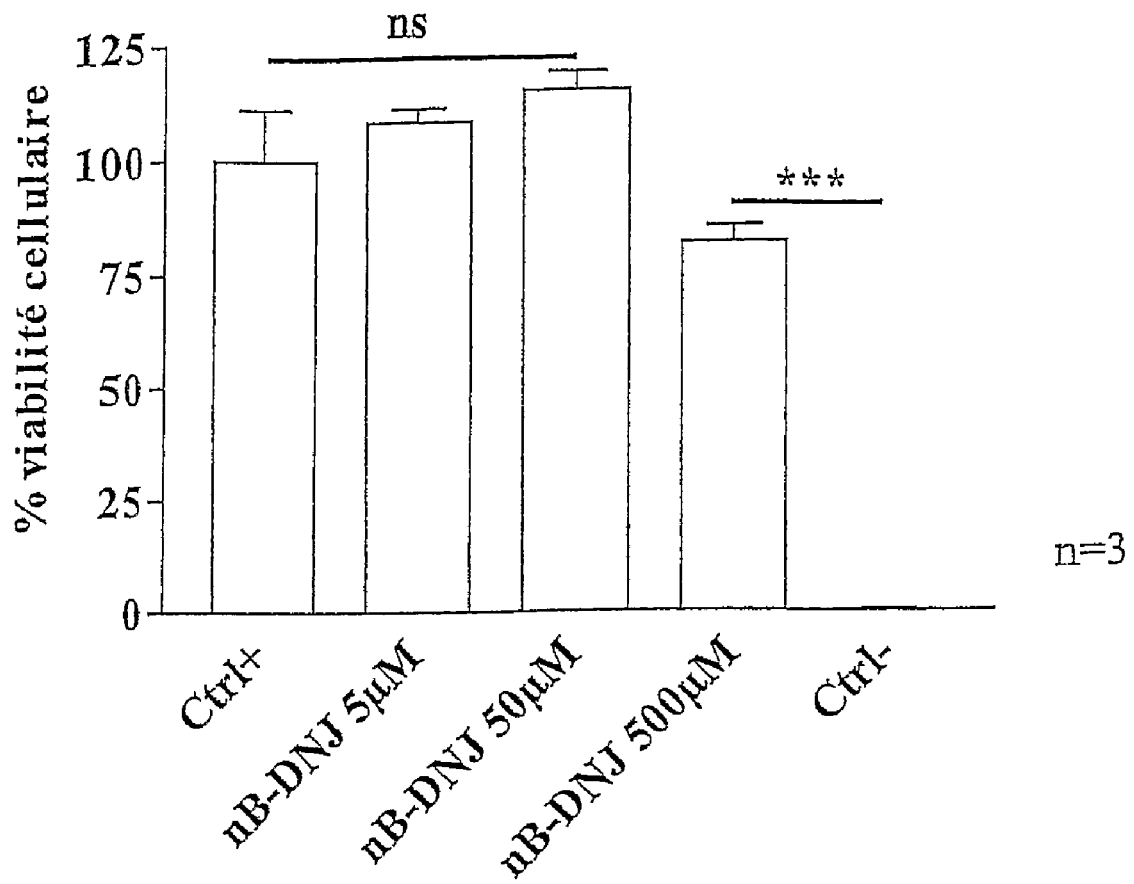

For the purpose of testing the cytotoxicity of NB-DNJ, CHO-WT cells were incubated for 2 hours with different concentrations of inhibitors before being subjected to the cell viability test with MTT. FIG. 5 shows a summary of the results. The results show that the cells are viable for all the concentrations of NB-DNJ. This molecule therefore exhibits no cell cytotoxicity.

R5. Effect of the NB-DNJ Analogues on the Addressing of delF508 in the CF15 Cells We compared the effects of different compounds of the N-butyl-deoxynojirimycin family (NB-DNJ or nB-DNJ). The products are presented in FIG. 6. For each experiment, the addition of a cocktail (Forskolin 10μM, Genistein 30μM) allows the activation of the CFTR when the latter is on the membrane. The results presented in FIG. 7 show that the treatment of the CF15 cells with 100μM of DNJ, nB-DMJ or DMJ for two hours at 37° C. restores an addressing of the delF508 protein and allows the latter to function as an ion transporter (FIG. 7). By contrast the compounds DGJ, nB-DGJ, DFJ and nB-DFJ have no significant effect on the addressing of delF508 (FIG. 7). For each compound (DNJ, DMJ and nB-DMJ) the $EC_{50}$ (concentration of the molecule which produces 50% of the maximum effectiveness) was determined at >250μM, 134μM and 113μM respectively.

III) CONCLUSIONS

The efflux tests revealed that the NB-DNJ causing an accumulation of the delF508 in the endoplasmic reticulum allows a membranous relocation of this protein and therefore represents an important pharmacological means of re-addressing the delF508 in a human pulmonary epithelial cell. The NB-DNJ allows the specific membrane addressing of delF508 without affecting the ion transporting activity of this protein, and has no effect on the other chloride channels, nor on the cell viability.

BIBLIOGRAPHY

BECQ et al. (1999) Journal of Biological Chemistry 274, 27415-27425.
CHENG et al. (1990) Cell 63, 827-834.
COX et al. (2000) The Lancet 355, 1481-1485.
DORMER et al. (2001) Journal of Cell Science 114, 4073-4081.
DWEK et al. (2000) Patent WO 00/62779
ELLGAARD & HELENIUS (2003). Molecular Cell Biology, 4, 181-191.
FIEDLER & SIMONS K. (1995) Journal of Cell Science 109, 271-276.
GELMAN et al. (2002) The Journal of Biological Chemistry 277, 11709-11714.
PLATT et al. (1994) The Journal of Biological Chemistry 269, 27108-27114.
PLATT et al. (2001) J. Inherit. Metab. Dis. 24, 275-290.
RIORDAN et al. (1989) Science 245, 1066-1073
TSUI et al. (1985) Science 230, 1054-1057.
WEI et al., (1996) Journal of Cellular Physiology, 168, 373-384.

LEGEND TO THE FIGURES

FIG. 1: Effect of NB-DNJ on the Addressing of delF508.

The CF15 cells were pre-treated for 2 hours with NB-DNJ (500μM). The effect of the MPB-91 (250μM) is considered as representing 100% in this test. The CFTR activity is measured in iodide efflux (n=8 for each condition) after stimulation by fsk 10μM+Gst 30μM. Ns: non-significant difference. ***: significant difference P<0.001

FIG. 2: Graph Showing Effect of NB-DNJ on the Addressing of delF508.

The CF15 cells were pre-treated for 2 hours with NB-DNJ at different concentrations. The CFTR activity is measured in iodide efflux (n=4 for each concentration) after stimulation with fsk 10μM+Gst 30μM.

Figure 3:
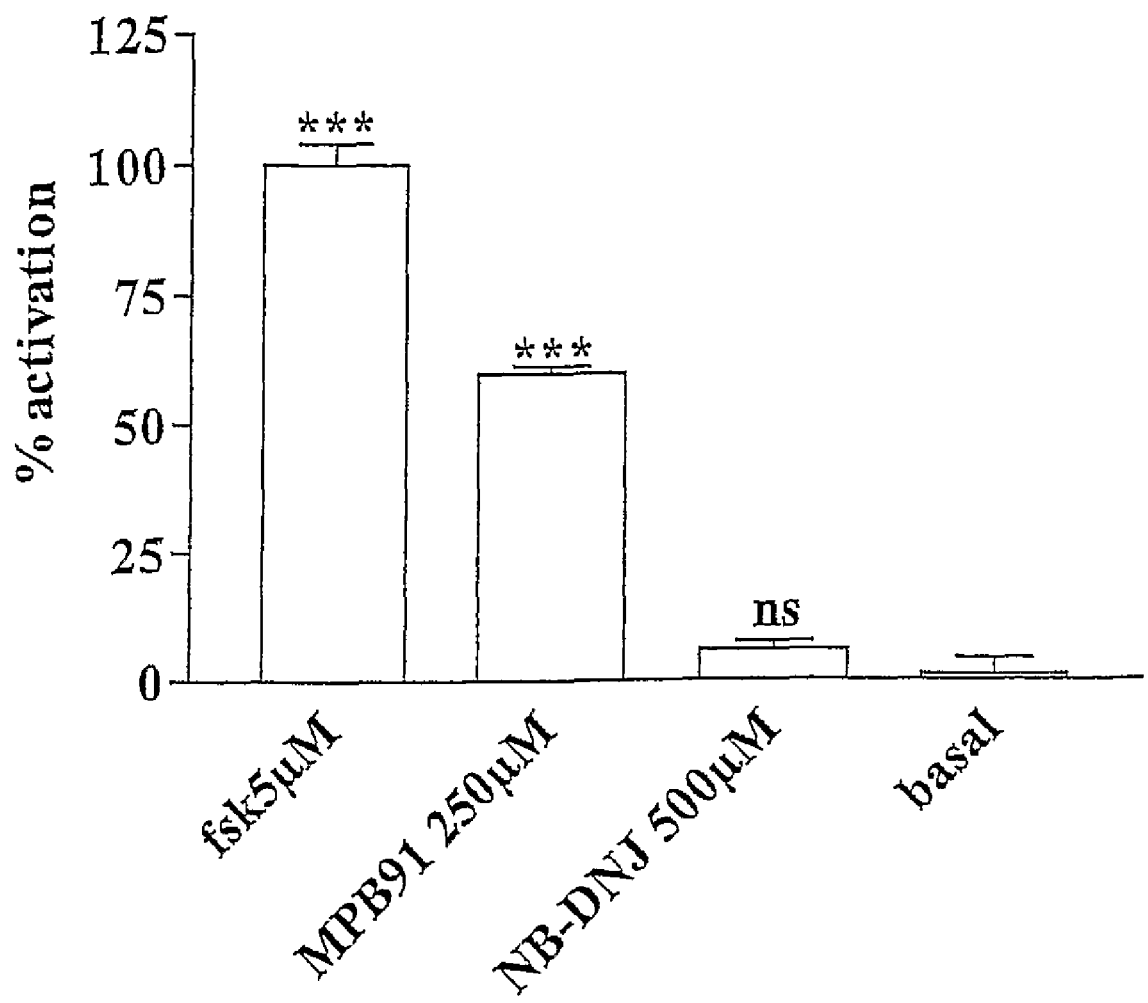

FIG. 3: Effect of NB-DNJ on the Anionic Transports of the Calu-3 Cells.

The CFTR activity is measured in iodide efflux (n=8 for each condition) after stimulation by forskolin (fsk) 5μM, MPB-91 250μM, NB-DNJ 500μM. It should be noted that the fsk and compound MPB-91 activate an iodide efflux in this cell, but not the NB-DNJ which has no effect. Ns: non-significant difference. ***: significant difference P<0.001

FIG. 4: Effect of a Treatment with NB-DNJ of the Calu-3 Cells.

The Calu-3 cells are pre-incubated for 2 hours at 37° with 500μM NB-DNJ, with MPB-91 250μM. Cells not treated: no treat. Basal indicates that the cells have been neither treated nor stimulated. The CFTR activity is measured in iodide efflux (n=8 for each condition) after stimulation by MPB-91 250μM. It should be noted that a treatment with NB-DNJ does not have any effect as the level of stimulation of the efflux is the same for the three conditions. Ns: non-significant difference.

FIG. 5: Effect of NB-DNJ on the Cytotoxicity of the CHO Cells.

It should be noted that at 5 and 50μM no cytotoxicity is measurable. A low toxicity appears at 500μM. 2 hours of treatment of the cells. Ns: non-significant difference. ***: significant difference P<0.001

Figure 6:
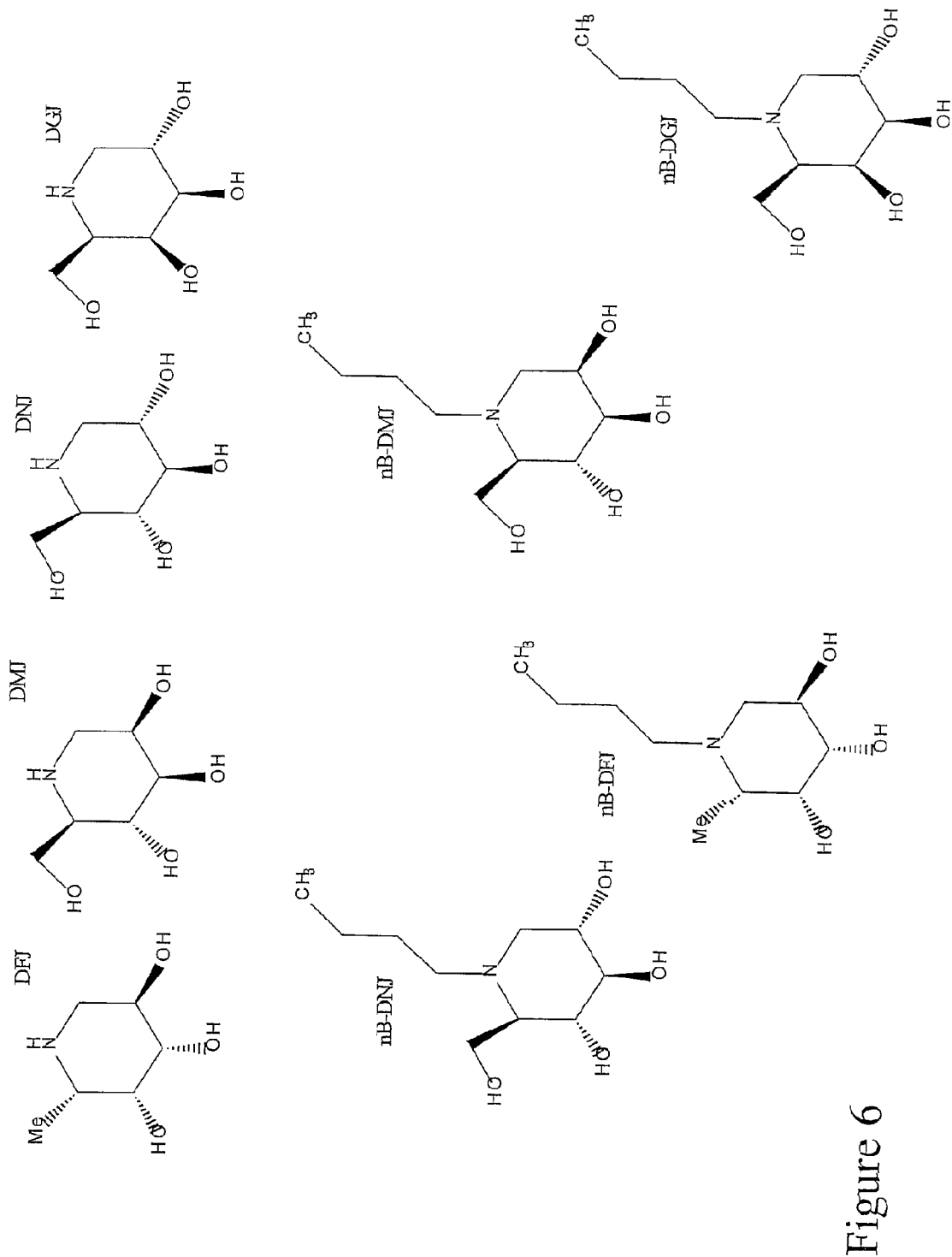
Figure 7:
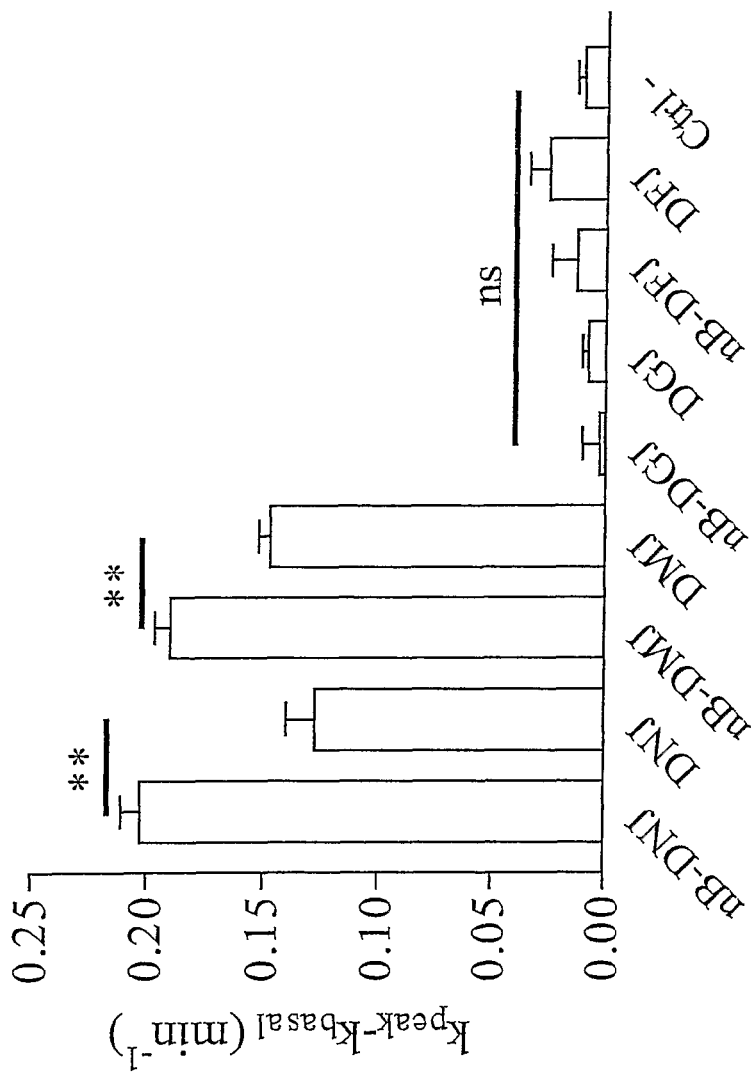

FIG. 6: Structures of N-butyl-deoxynojirimycin (NB-DNJ or nB-DNJ) and the Different Compounds of the NB-DNJ Family.

FIG. 7: Effect of NB-DNJ and Analogues of NB-DNJ on the Addressing of delF508 in the CF15 Cells

The invention claimed is:

1. A method for the treatment of cystic fibrosis, comprising administering to a subject in need thereof a pharmaceutically acceptable amount of a glucosidase inhibitor, wherein said inhibitor is a compound having the following formula:

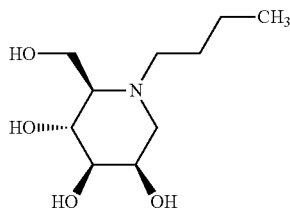

NB-DMJ (N-butyldeoxymannojirimycin).

2. The method of claim 1, wherein the inhibitor is administered by oral, rectal or nasal route.

3. The method of claim 1, wherein the inhibitor is administered in an amount of 1 mg to 2 g per day for adults, or 1 mg to 1 g per day for children and infants, in one or more doses.

4. The method of claim 1, wherein the inhibitor is administered in a form selected from the group consisting of: syrup, suspension, gelatine capsules, tables, powder, granules, suppositories, aerosol by inhalation, and drops.

* * * * *